(12) United States Patent
Streed et al.

(10) Patent No.: US 11,867,606 B1
(45) Date of Patent: Jan. 9, 2024

(54) AIR QUALITY SENSOR SYSTEM

(71) Applicant: CRS Industries, Inc., Concord, NC (US)

(72) Inventors: Eric Streed, Dunwoody, GA (US); Dustin Aumock, Camden, SC (US); Daniel F Cox, Camden, SC (US)

(73) Assignee: CRS Industries, Inc., Concord, NC (US)

( * ) Notice: Subject to any disclaimer, the term of this patent is extended or adjusted under 35 U.S.C. 154(b) by 172 days.

(21) Appl. No.: 17/246,687

(22) Filed: May 2, 2021

Related U.S. Application Data

(60) Provisional application No. 63/019,688, filed on May 4, 2020.

(51) Int. Cl.
*G01N 15/14* (2006.01)
*G01N 33/00* (2006.01)
*G01N 1/24* (2006.01)

(52) U.S. Cl.
CPC .......... *G01N 15/1434* (2013.01); *G01N 1/24* (2013.01); *G01N 33/004* (2013.01); *G01N 33/0047* (2013.01); *G01N 2001/245* (2013.01); *G01N 2015/1486* (2013.01)

(58) Field of Classification Search
CPC ................................................. G01N 15/1434
USPC ......................................................... 73/28.01
See application file for complete search history.

(56) References Cited

U.S. PATENT DOCUMENTS

| 2016/0063833 A1* | 3/2016 | Schultz | G08B 19/00 340/522 |
| 2019/0025180 A1* | 1/2019 | Yang | G01N 15/06 |

FOREIGN PATENT DOCUMENTS

| JP | 2017166935 A | * | 9/2017 | ........... G01J 1/42 |
| WO | WO-2018152239 A1 | * | 8/2018 | ......... G01N 15/0205 |

OTHER PUBLICATIONS

Kawai. Translation of JP-2017166935-A. Published Sep. 2017. Accessed Dec. 2022. (Year: 2017).*

* cited by examiner

*Primary Examiner* — Walter L Lindsay, Jr.
*Assistant Examiner* — Philip T Fadul
(74) *Attorney, Agent, or Firm* — Frijouf, Rust & Pyle P.A.

(57) ABSTRACT

An air quality sensor system is disclosed comprising a housing defining a sidewall means. An air input is located on a first sidewall of the sidewall means with an air output located on a second sidewall of the sidewall means angularly disposed relative to the first sidewall of the sidewall means. A particle sensor including a fan is located within the housing and interposed between the air input and the output for sensing the number of particles passing between the air input and the air output. Preferably, a temperature and humidity sensor, a volatile organic compound (VOC) sensor and a carbon dioxide ($CO_2$) sensor are provided for sensing the ambient air. A transmitter may be included for transmitting data from the particle sensor.

18 Claims, 8 Drawing Sheets

AIR QUALITY SENSOR SYSTEM

BACKGROUND OF THE INVENTION

Field of the Invention

The invention relates to air purification measurement and control and more particularly to an improved air quality sensor purification system for measuring the quality of environmental air and/or controlling an air conditioning/heating system.

Description of the Related Art

Air quality and air purification have been concerns since the early 1800s. Through the years, scientists continued to develop more sophisticated and effective systems to achieve cleaner air. Today, commercial air purification systems which may be installed as stand-alone units or incorporated into an air handler or HVAC unit are commonly found in medical, commercial and industrial buildings. The purpose of every commercial air purification system is to eliminate airborne contaminants such as pollen, dust, mold spores and other harmful contaminates from the occupied space. However, many conventional air filtration systems are unable to capture particles in the micron and sub micron range in the occupied space. Enhanced particle removal has been achieved using purification systems which subject airborne contaminants to complex electrical fields so contaminates can be transported by air to be captured by a filter for removal from the occupied space. Since these contaminates are not visible, there is a requirement for accurately measuring each critical contaminate in the occupied space to assure that the air purification systems are performing as specified.

Air purification systems reduce energy costs by air recirculation, thereby reducing the need for large amounts of outside air. The re-circulated air remains close to the desired interior space temperature thereby reducing the need for additional heating or cooling of the air passing through the HVAC.

Although the development of air purification systems has been primarily directed to units installed in commercial buildings and the like, there remains the need for high efficiency air purification systems for residential applications.

There have been many in the prior art who have addressed these problems with high levels of success. The following U.S. Patents are representative of the prior art addressing this problem.

U.S. Pat. No. 3,862,826 to Haupt discloses a filter system for removing pollutant particles suspended in a fluid body. The system comprising a precharging means to electrically precharge the suspended particles, and a precipitator means to attract and collect the charged particles. A fluid turbulator means disposed between the precharging means and precipitator means alters the fluid flow to enhance the collection of the charged particles and neutralizing means neutralizes the fluid flow before exiting the filter system U.S. Pat. No. 3,892,544 to Haupt discloses an electrodynamic electrostatic gas charge system to separate combined particles of dissimilar substances and recombination into combined particles of similar substance. The system comprises an antenna array including a first and second electrode means disposed across the gas flow and a signal generator means. The signal generator means includes a first and second signal output generator means coupled to the first and second electrode means respectively to generate charged force fields to separate dissimilar substances and recombine like particles.

U.S. Pat. No. 3,977,848 to Oliphant discloses an electrodynamic gas charge system comprising at least one electrically charged element and screen element arranged relative to each other to form a voltage gradient therebetween. The system includes means to vary the voltage gradient between the electrically charged element and screen element. The elements are disposed across a gas flow such that particles of dissimilar substances are separated by the charged force field and recombined with like particles.

U.S. Pat. No. 4,019,367 to Norsworthy discloses an improved method and apparatus for the detection and measurement of concentrations of foreign substances in a fluid, particularly atmospheric gas. Transducers and signal modifying devices are electronically connected in a predetennined arrangement so as to determine the concentration of foreign matter and display this concentration as a linear function determined by the amount of foreign matter found.

U.S. Pat. No. 5,061,296 to Sengpiel, et al. discloses an air purification system for subjecting air to a complex electrical field including sensors and a monitor/controller for monitoring effectiveness, operational conditions of the electrical field and the system, and ambient conditions of the air being purified. The level of the high voltage, RMS and high frequency is processed so that frequency. RMS and high D.C. can be measured at a low D.C. voltage.

U.S. Pat. No. 5,542,964 to Kroeger, et al. discloses an air purification system where air is subjected to complex electrical field resulting from a DC voltage and AC frequency in kilovolt and kilohertz range respectively, applied to screen assembly in air path. DC amplitude and AC frequency self regulate to selected parameters. Parameters are selectable independently of one another.

U.S. Pat. No. 5,542,964 to Kroeger, et al. discloses an air purification system where air is subjected to complex electrical field resulting from a DC voltage and AC frequency in kilovolt and kilohertz range respectively, applied to screen assembly in air path. DC amplitude and AC frequency self regulate to selected parameters. Parameters are selectable independently of one another.

U.S. Pat. No. 10,155,228 to Eric Bratton discloses an improved ceiling mounted air treatment system for installation upon a ceiling grid system having a plurality of ceiling panels within a room. The improved ceiling mounted air treatment system comprises a ceiling plenum defining a plurality of side walls, a top wall and a bottom wall. The plurality of side walls are dimensioned for replacing a ceiling panel of the ceiling grid system. An air input and an air output are defined in the bottom wall. A grid array is disposed within the plenum and located between the air input and the air output. An electronic generator is connected to the grid array for treating the flow of air through the grid array. A fan is interposed between the air input and the air output for establishing the flow of air from the room into the air input to exit from the air output into the room.

U.S. Pat. No. 10,183,299 to Eric Bratton discloses an input plenum for mounting to an air conditioning/heating unit. The input plenum comprises an air filter track for introducing and removing the air filter. A grid array track is located within the input plenum. The grid array track enables a grid array and an electronic generator to be added to the plenum to upgrade the plenum into an air purification system. An improved one-piece grid may be incorporated into the grid array for generating an electric field in the air purification system.

The universal standard for indoor air quality (IAQ) is the 2.5-micron, or micrometer. This 2.5-micron baseline, commonly referred to as PM 2.5 refers to particulates that are two and one-half microns or less in width. The measurement for PM 2.5 is the concentration of these microscopic particles less than 2.5 microns per cubic meter.

The above prior art devices improve indoor air (IAQ) by enhancing and accelerating sub-micron (2.5 microns and smaller) particulate to agglomerate or coagulate into larger particles that can be captured by conventional filters. This technology has been tested for nearly 50 years by independent consultants and laboratories to prove the technology effectively removes particulate in the 2.5-micron size range and smaller. Furthermore, the above prior art devices produce no ozone.

While there are many known and measured contaminates of concern, from radon to exhaust fumes (VOC's), a contaminate of primary concern focuses on carbon dioxide ($CO_2$). $CO_2$ has historically been considered the trace contaminate that represents the preponderance of all other contaminates of concern. The negative effects of $CO_2$ are well known, from drowsiness (starting at levels of 1100 ppm) to unconsciousness and even death (at levels above 5000 ppm).

There is a need in the art for a low-cost portable sensor for sensing the undesirable presence of excessive particles in the 2.5-micron size range and smaller as well as the undesirable presence of excessive amounts of carbon dioxide (CO).

Therefore, it is an object of the present invention to provide an air quality sensor system for sensing the presence of particle suspended in the air having a 2.5-micron size range.

Another object of this invention is to provide an air quality sensor system for sensing the presence of excessive amounts of carbon dioxide ($CO_2$).

Another object of this invention is to provide an air quality sensor system to continuously monitor the presence of particle suspended in the air having a 2.5-micron size range.

An additional object of this invention is to provide an air quality sensor system to continuously monitor the presence of carbon dioxide ($CO_2$).

Another object of this invention is to provide an air quality sensor system to continuously monitor the presence of volatile organic compounds (VOC).

Another object of this invention is to provide an air quality sensor system that provides a controlled air flow over and through a particle counter.

Another object of this invention is to provide an air quality sensor system that provides alerts and alarms upon an excessive amount of particles suspended in the air having a 2.5-micron size range, or excessive levels of $CO_2$ and VOC's.

Another object of this invention is to provide an air quality sensor system that transmits data history and analytics tools to a remote location.

Another object of this invention is to provide an air quality sensor system that may be located at remote positions throughout an occupied space.

Another object of this invention is to provide an air quality sensor system that may be linked to an air conditioning/heating system.

Another object of this invention is to provide air quality sensor system that is simple to install by an installer with limited skills.

Another object of this invention is to provide an air quality sensor system that is simple for the operator to use.

Another object of this invention is to provide an air quality sensor system that is cost effective to produce.

The foregoing has outlined some of the more pertinent objects of the present invention. These objects should be construed as being merely illustrative of some of the more prominent features and applications of the invention. Many other beneficial results can be obtained by modifying the invention within the scope of the invention. Accordingly other objects in a full understanding of the invention may be had by referring to the summary of the invention, the detailed description describing the preferred embodiment in addition to the scope of the invention defined by the claims taken in conjunction with the accompanying drawings.

SUMMARY OF THE INVENTION

The present invention is defined by the appended claims with specific embodiments being shown in the attached drawings. For the purpose of summarizing the invention, the invention relates to an air quality sensor system is disclosed comprising a housing defining a sidewall means. An air input is located on a first sidewall of the sidewall means with an air output located on a second sidewall of the sidewall means angularly disposed relative to the first sidewall of the sidewall means. A particle counter including a fan is located within the housing and interposed between the air input and the output for sensing the number of particles passing between the air input and the air output. A transmitter may be included for transmitting data from the particle counter.

In a more detailed example, the sidewall means comprises a quadrilateral housing with the second sidewall of the sidewall means disposed perpendicular to the first sidewall of the sidewall means. The housing includes a front end and a rear end with a dividing wall located intermediate the front end and the rear end. The housing includes a front end and a rear end with a dividing wall located intermediate the front end and the rear end and a front cover a rear cover for covering the front end and the rear end of the housing.

In another detailed example, the air input includes an input tunnel communicating the air input to the particle counter and the air output includes an output tunnel communicating the particle counter to the air output. The air input may include a linear input tunnel communicating the air input to the particle counter whereas the air output may include a curved output tunnel communicating the particle counter to the air output.

Preferably, the particle counter includes a laser for counting particles passing between the air input and the air output. A temperature and humidity sensor, a VOC sensor and a carbon dioxide ($CO_2$) sensor may be located remote from the first and second sidewalls for sensing ambient air. The air quality sensor system includes an indicator for indicating an undesired count of particles suspended within the air and/or abnormal temperature, and/or volatile organic compounds (VOC), and/or carbon dioxide ($CO_2$). A temperature and humidity sensor, a volatile organic compound (VOC) sensor, and a carbon dioxide ($CO_2$) sensor may be located remote from the first and second sidewalls for sensing ambient air. A transmitter transmits data from the particle counter and the temperature and humidity sensor, a volatile organic compound (VOC) sensor, and a carbon dioxide ($CO_2$) sensor.

In another embodiment, the invention is incorporated into an air quality sensor system comprising a quadrilateral housing having first through fourth sidewalls with a second sidewall disposed perpendicular to a first sidewall. An air input is located in the first sidewall and an air output is located in the second sidewall. A particle counter including a fan is located within the housing and interposed between the air input and the air output for sensing the number of particles passing between the air input and the air output.

In a more specific example of the invention, the air input includes a linear input tunnel communicating the air input to the particle counter and the air output includes a curved output tunnel communicating the particle counter to the air output. The curved output tunnel has cross-sectional area greater than the linear input tunnel.

The particle counter includes a laser for counting particles passing between the air input and the air output. A temperature and humidity sensor, a volatile organic compound (VOC) sensor, and a carbon dioxide ($CO_2$) sensor is located remote from the first and second sidewalls for sensing ambient air. An indicator indicates an undesired count of particles suspended within the air and/or the temperature, the volatile organic compound (VOC) sensor, and the carbon dioxide ($CO_2$) content within the air. A transmitter transmits data from the air quality sensor system to a remote location The housing includes a front end and a rear end with a dividing wall located intermediate the hont end and the rear end. The particle counter comprises a laser located on one surface of the dividing wall for counting particles passing between the air input and the air output. A transmitter is located on a second surface of the dividing wall for transmitting data from the particle sensor.

The housing includes a front end and a rear end with a dividing wall located intermediate the front end and the rear end. The particle counter comprises a laser located on one surface of the dividing wall for counting particles passing between the air input and the air output. A transmitter is located on a second surface of the dividing wall for transmitting data from the particle sensor. A front cover and a rear cover enclose the front end and the rear end of the housing.

The foregoing has outlined rather broadly the more pertinent and important features of the present invention in order that the detailed description that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be made to the following detailed description taken in connection with the accompanying drawings in which.

Similar reference characters refer to similar parts throughout the several Figures of the drawings.

DETAILED DISCUSSION

Figure 1:
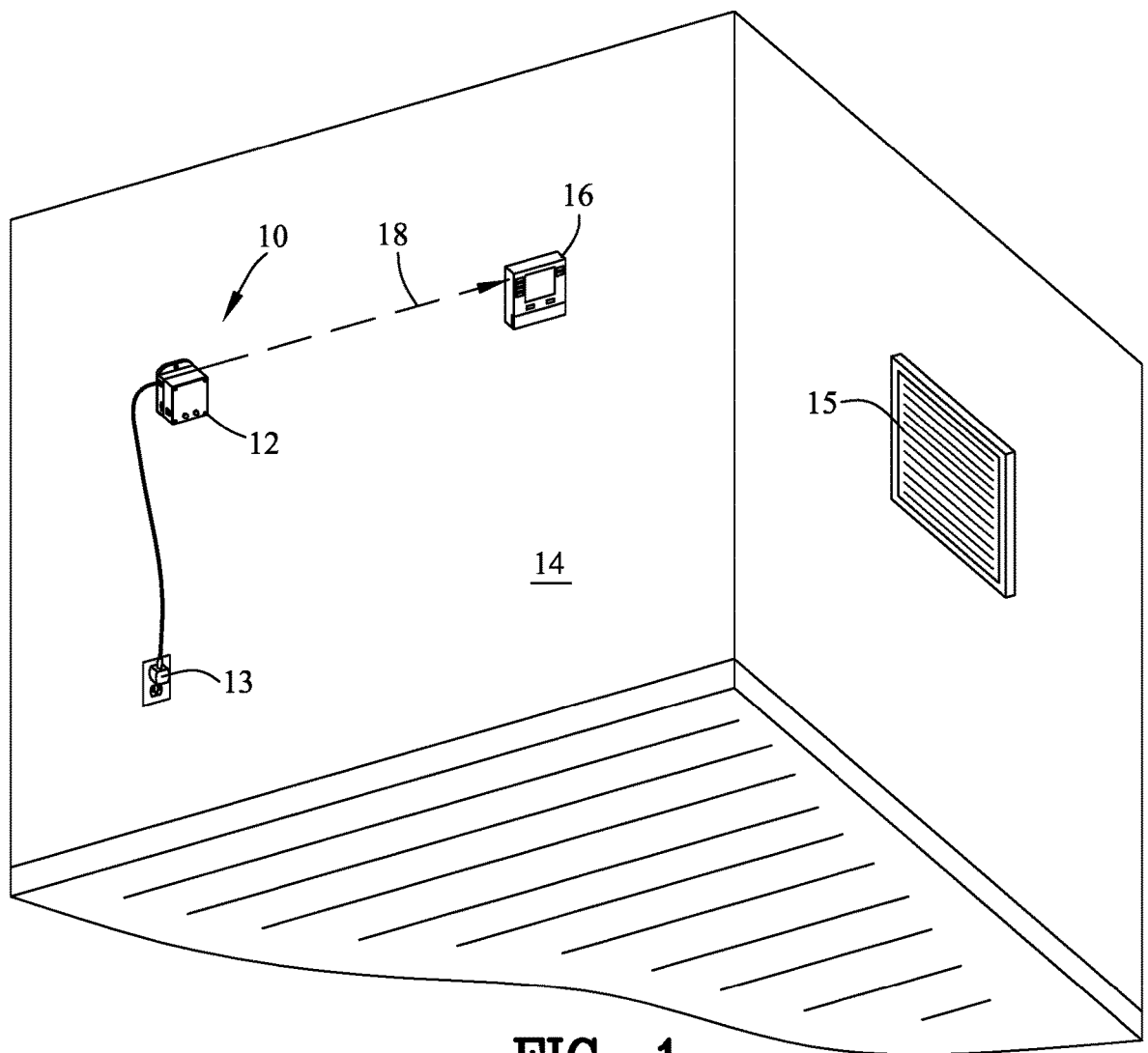
FIG. 1 is an isometric view of the air quality sensor system of the present invention mounted in an air conditioned and heated room.
Figure 3:
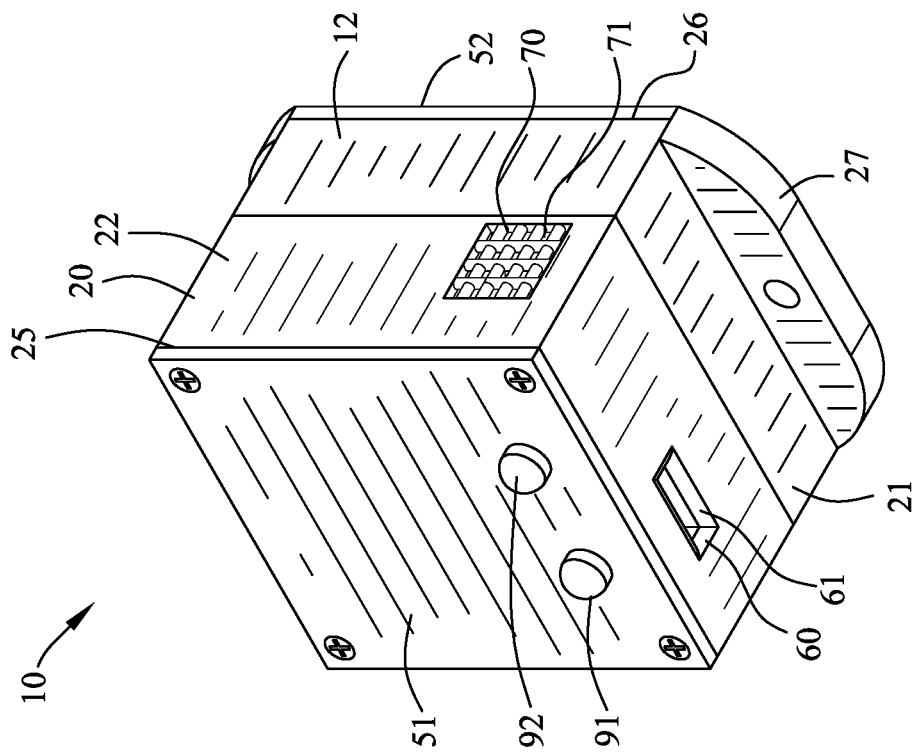
FIG. 3 is an enlarged bottom right left isometric view of the air quality sensor system of the present invention shown in of FIG. 1.
Figure 2:
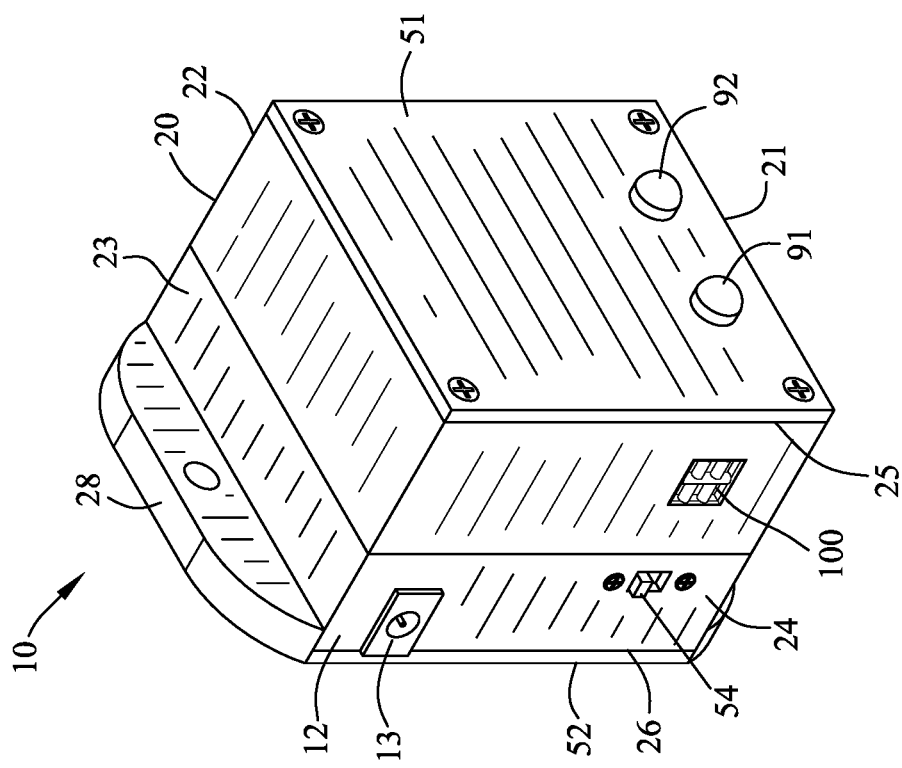
FIG. 2 is an enlarged top right isometric view of the air quality sensor system of the present invention shown in FIG. 1.
Figure 5:
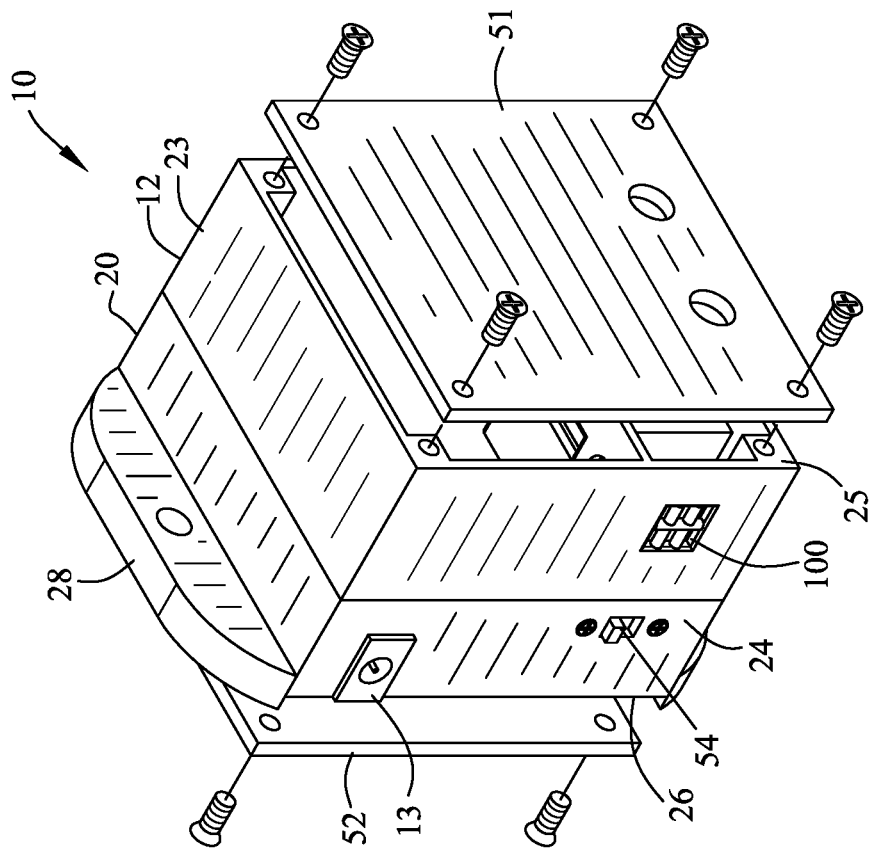
FIG. 5 is a view similar to FIG. 2 with the front and rear covers being removed.
Figure 4:
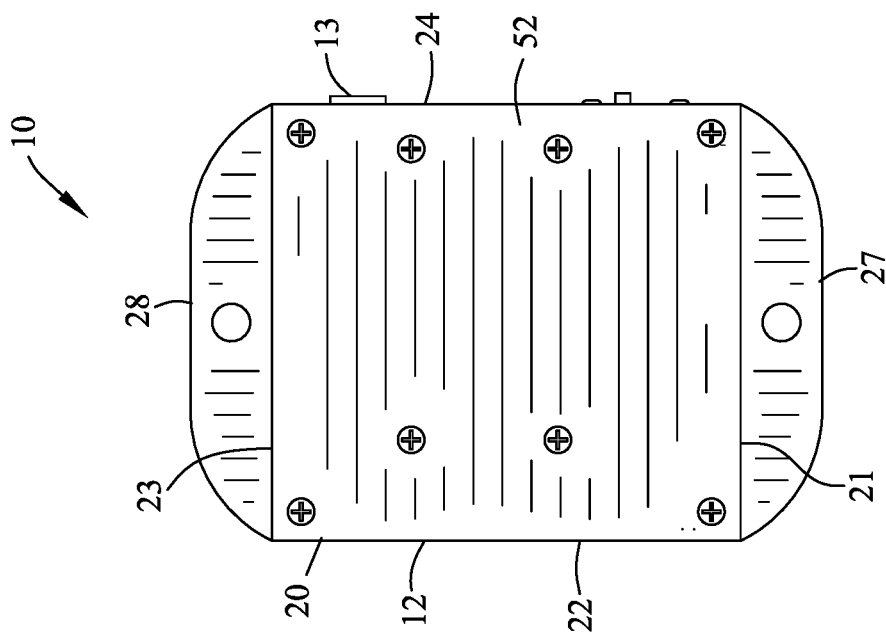
FIG. 4 is a rear view of the air quality sensor system shown in FIGS. 2 and 3.

FIG. 1 is an isometric view of the air quality sensor system 10 of the present invention. The air quality sensor system 10 is contained within a housing 12 and is powered by a low voltage power supply 13. The air quality sensor system 10 is mounted in a room 14 at a position to sense the ambient air within the room 14. An air conditioned and heating system 15 provides cool or heated air within the room 14. Preferably, the air conditioning and heating system 15 is constructed in accordance with the aforementioned prior art incorporating an effective filtering system. The air conditioning heating system 15 is controlled by thermostat 16. Preferably, the air quality sensor system 10 of the present invention is coupled to the thermostat 16 by wireless connection as indicated by the arrows 18 as will be described in greater detail hereinafter.

FIGS. 2-10 illustrate various views of the air quality sensor system 10 of the present invention. The housing 12 of the air quality sensor system 10 is defined by sidewall means 20 shown as a quadrilateral housing having first through fourth sidewalls 21-24. The second sidewall 22 is disposed perpendicular to the first sidewall 21. Although the sidewall means 20 of the housing 12 has been shown as a quadrilateral housing, it should be appreciated that the housing 12 may take various shapes such as a cylindrical shape or a prism shape having multiple sides depending upon the desired appearance of the housing 12. The overall shape of the housing 12 is a matter of aesthetic design so long as a second side 22 is disposed in an angular relationship relative to a first side 21 of the housing 12. The housing 12 includes a front end 25 and a rear end 26. Flanges 27 and 28 extend from the housing for mounting the air quality sensor system 10.

FIGS. 11-15 illustrate various views of the housing 12 with the components of the air quality sensor system 10 with front and rear covers 51 and 52 removed from the housing 12. A dividing wall 30 is located between the front end 25 and the rear end 26. The dividing wall 30 has a first and a second side 31 and 32 defining a front region 41 and a rear region 42. An orifice 43 extends through the dividing wall 30 to provide communication between the front region 41 and the rear region 42.

A secondary wall 44 separates the front region 41 into a first space 45 and a second space 46. The secondary wall 44 is orientated perpendicular to the dividing wall 30. An orifice 47 extends through the separating wall 44 to provide communication between the first space 45 and the second space 46. Preferably, the dividing wall 30 and the secondary wall 44 are molded integrally molded with the sidewalls 21-24. A front cover 51 and a rear cover 52 enclose the front region 41 and the rear region 42 of the housing 12.

It should be appreciated by those skilled in the art that the terms front, rear and wall as set forth above described the housing 12 mounted on a vertical surface such as a wall as shown in FIG. 1. However, the housing 12 may be mounted on a horizontal surface with the front end 25 and an upward facing position on a table (not shown) or the like or a downward facing position when the housing 12 is located a ceiling (not shown).

An air input 60 and an air output 70 are located on the sidewall 21 with the air output 70 located on the second sidewall 22 of the sidewall means 20 angularly disposed relative to the first sidewall 21 of the sidewall means 20. In the example, the second sidewall 22 disposed perpendicular relative to the first sidewall 21.

The air input 60 located on the first sidewall 21 of the sidewall means 20. The air input 60 is shown extending between an outer end 61 and an inner end 62 forming an input tunnel 64. The outer end 61 is connected to the sidewall 21 whereas the inner end 62 is connected to the secondary wall 44. The air input tunnel 64 is a linear input tunnel communicating the air input 60 to an output 66 defined in the secondary wall 44. The air input tunnel 64 defines a cross-sectional area 68.

The air output 70 located on the second sidewall 22 of the sidewall means 20. The air output 70 is shown extending between an outer end 71 and an inner end 72 forming an output tunnel 74. The outer end 71 is connected to the sidewall 22 whereas the inner end 72 is connected to the secondary wall 44. The air output tunnel 74 is a curved output tunnel communicating the air output 70 to the output 66 defined in the secondary wall 44. The air output tunnel 74 defines a cross-sectional area 78.

The cross-sectional area 78 of the air output tunnel 74 is greater than the cross-sectional area 68 of the air input tunnel 64. In this example, the air output tunnel 74 has a cross-sectional area 78 five (5) times the cross-sectional area 68 of the air input tunnel 64. This ratio ensures a continuous and directed air flow from the room 14 through the input tunnel 64 into a particle sensor 80 to be exhausted from the output tunnel 74 into the room 14.

Referring back to FIGS. 6-10, the particle counter 80 is located with the second space 46 of the front region 41 of the housing 12. The particle counter 80 has an air input 81 and an air output 82 with a laser particle sensor 84 disposed therebetween.

The air input 81 and an air output 82 of the particle counter 80 is coupled to the air input tunnel 64 and the air output tunnel 74. A fan 86 is located within the particle counter 80 to provide a continuous and measured stream of air from the air input 81 to the air output 82. The continuous and measured stream of air from the air input 81 to the air output 82 is required to ensure that the laser particle sensor 84 accurately measures the particles within the 2.5-micron size range. The ratio of the air output tunnel 74 cross-sectional area 78 to the air input tunnel 64 cross-sectional area 68 is selected to maintain the continuous and measured stream of air required by the particle counter 80.

An electrical cable 88 extends through the orifice 43 in the dividing wall 31 to connect the particle counter 80 to an electronic circuit 90 located in the rear region 42 of the housing 12. The function of the electronic circuit 90 will be discussed in greater detail hereinafter.

An aperture 100 is located remote from the air input 60 and the air output 70. In this example, the aperture 100 is defined in the fourth sidewall 24 of the housing 12. The aperture 100 is located remote from the air input 60 and the air output 70 in order to avoid the air flow into and out of the housing 12. A solid-state sensor located adjacent to the aperture 100. The solid-state sensor comprises a temperature and humidity sensor 103 and a combined carbon dioxide ($CO_2$) sensor and a volatile organic compounds (VOC) sensor 104. An electrical cable 106 extends through the orifice 47 in the separating wall 44 to connect the sensors 103 and 104 to the electronic circuit 90 located in the rear region 42 of the housing 12.

Figure 6:
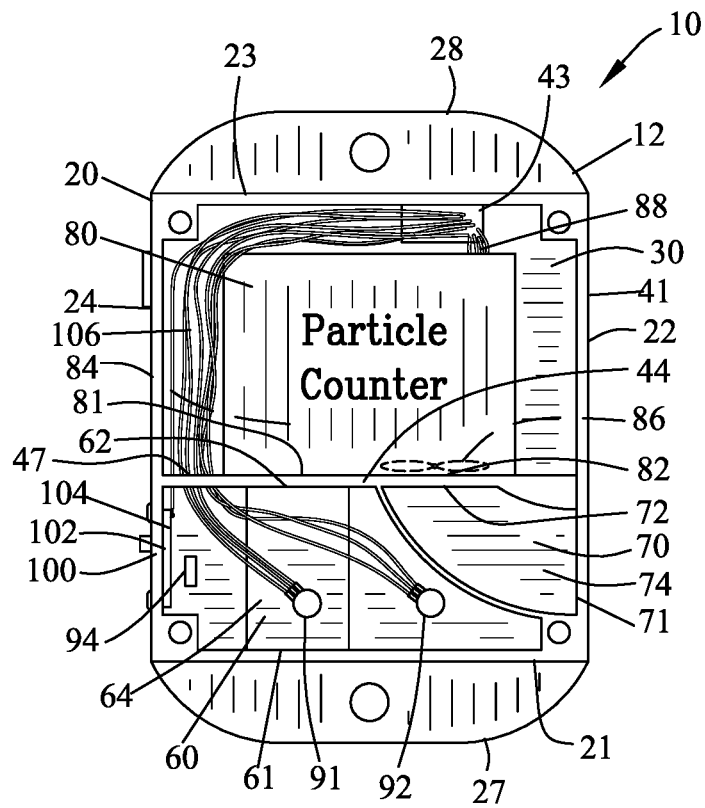
FIG. 6 is a front view of FIG. 5 with the front cover removed.
Figure 7:
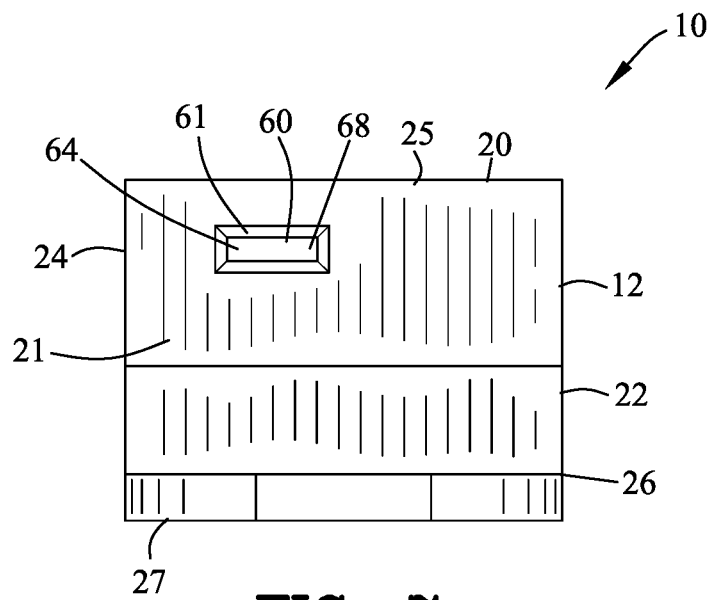
FIG. 7 is bottom view of FIG. 6.
Figure 8:
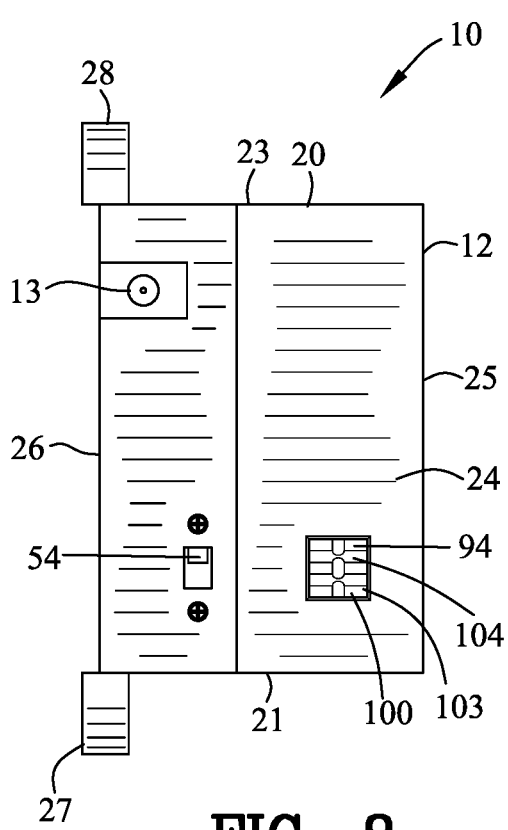
FIG. 8 is a left side view of FIG. 6.
Figure 9:
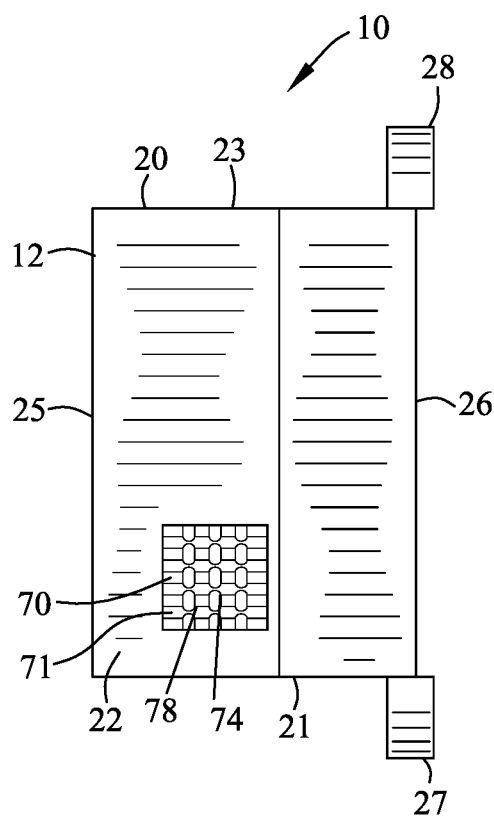
FIG. 9 is a right side view of FIG. 6.
Figure 10:
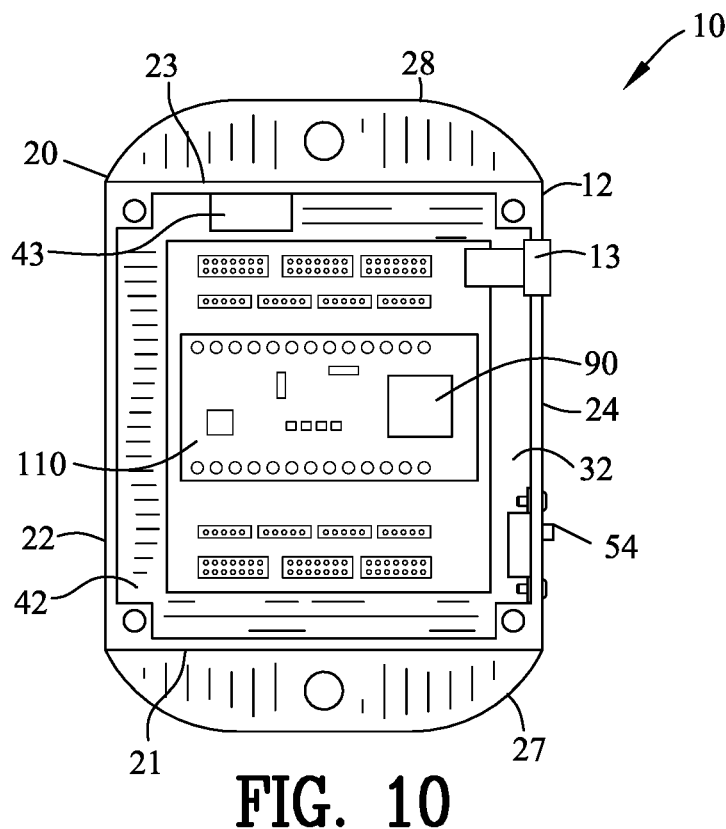
FIG. 10 is a rear view of FIG. 6 with the rear cover removed.
Figure 12:
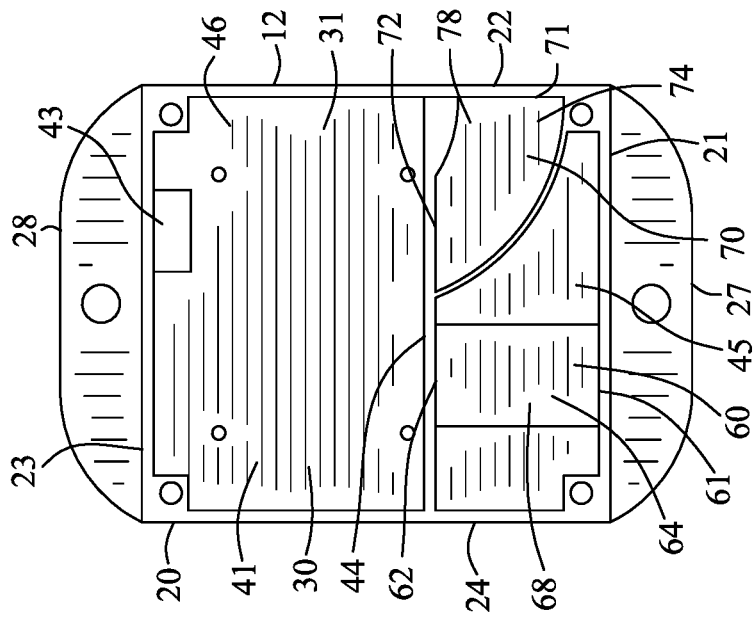
FIG. 12 is a view similar to FIG. 6 with the front cover removed showing only the housing of the air quality sensor system.
Figure 11:
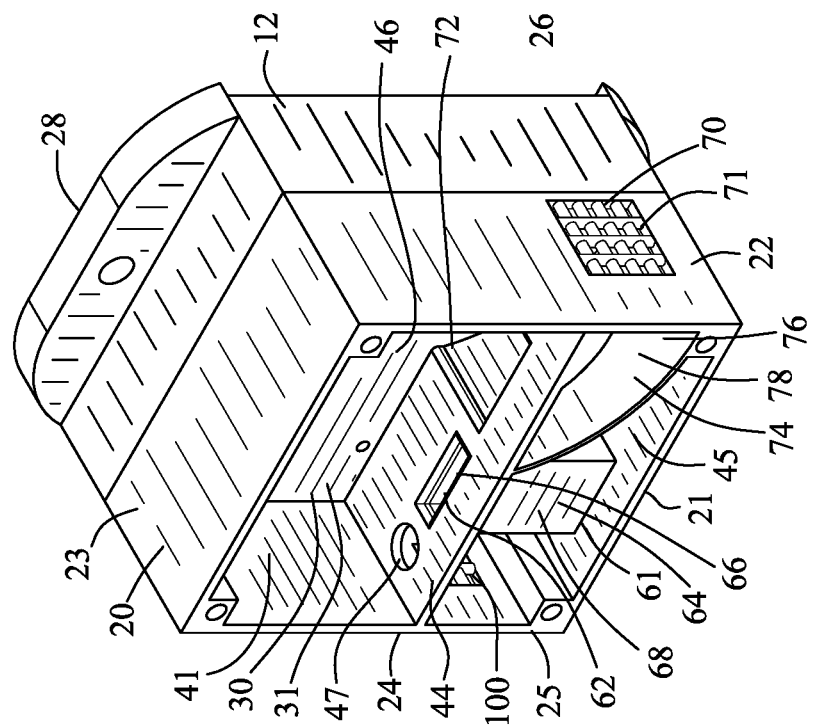
FIG. 11 is a view similar to FIG. 2 with the front cover removed showing only the housing of the air quality sensor system.
Figure 13:
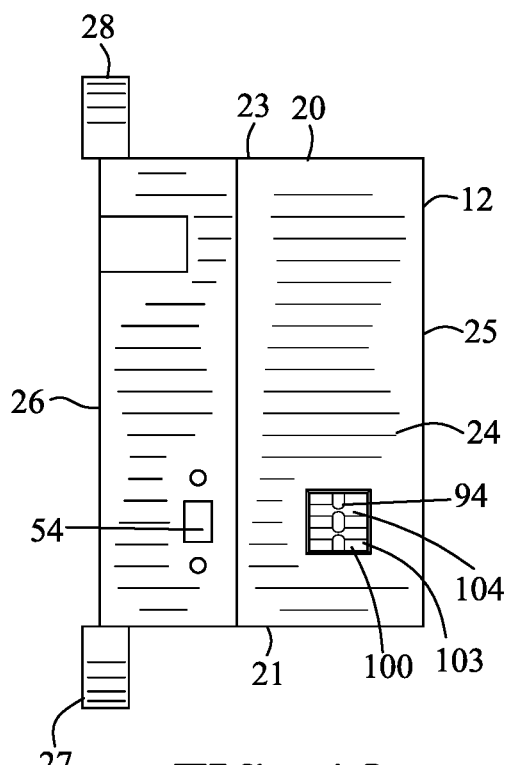
FIG. 13 is a view similar to FIG. 8 showing only the housing of the air quality sensor system.
Figure 14:
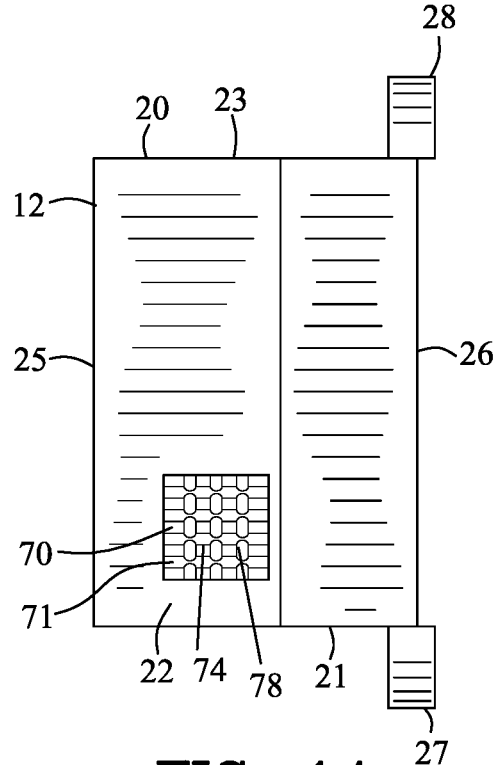
FIG. 14 is a view similar to FIG. 9 showing only the housing of the air quality sensor system.
Figure 15:
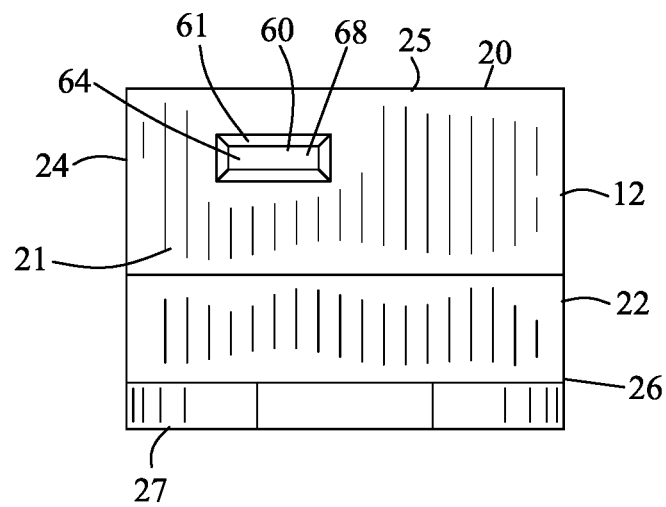
FIG. 15 is a view similar to FIG. 7 showing only the housing of the air quality sensor system.
Figure 16:
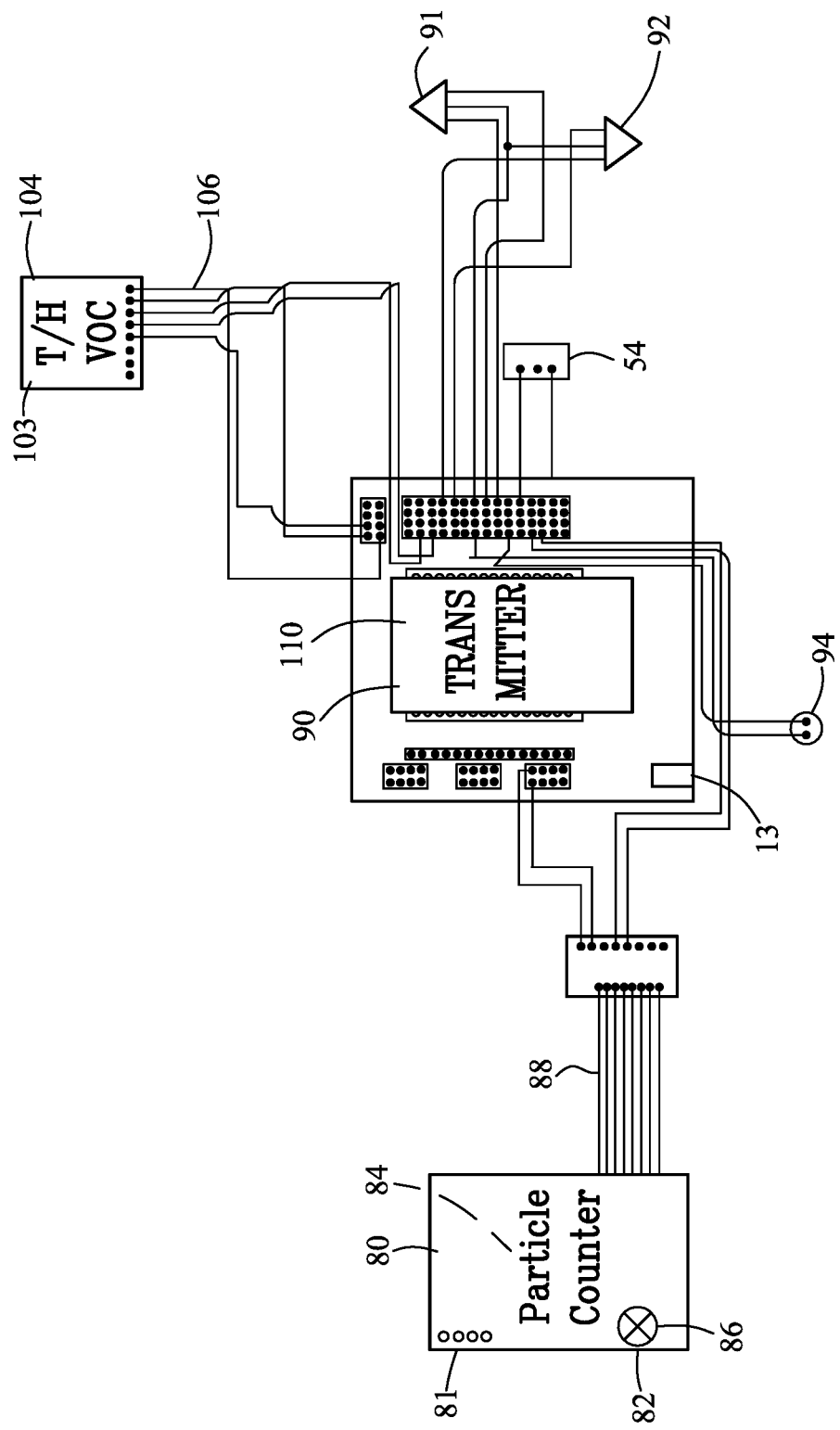
FIG. 16 is a block diagram of the electronic circuit of the air quality sensor system.

FIG. 16 is a block diagram of the electronic circuit 90 located in the rear region 42 of the housing 12 in FIG. 6. The electronic circuit 90 is connected to the indicators 91 and 92 located on the front cover 51 as well as an audible alarm 94 located adjacent to the aperture 100. The electronic circuit 90 collects data from the particle counter 80 and the solid-state temperature and humidity sensor 103 and carbon dioxide ($CO_2$) sensor 104.

The indicator 91 displays the condition of the level of carbon dioxide ($CO_2$) and/or the volatile organic compound (VOC) sensor. Preferably, the indicator 91 is a multicolored light emitting diode (LED). A green display indicated a safe level of carbon dioxide ($CO_2$) and/or volatile organic compounds (VOC) less than 1000 ppm. A yellow display indicated an unsafe level of carbon dioxide ($CO_2$) and/or volatile organic compound (VOC) greater than 1000 ppm. A red display indicated a hazardous level of carbon dioxide ($CO_2$) and/or volatile organic compound (VOC) greater than 2000 ppm.

The indicator 92 displays the condition of the level of particulate matter within the air based on the 2.5 micron universal standard for indoor air quality (IAQ). Preferably, the indicator 92 is a multicolored light emitting diode (LED). A green display indicated a safe level of 2.5 micron particles present in the air. A yellow display indicated an unsafe level of 2.5 micron particles and a red display indicated a hazardous level of 2.5 micron particles.

The electronic circuit 90 is connected to the indicators 91 and 92 located on the front cover 51 as well as an audible alarm 94 located adjacent to the aperture 100. The alarm 94 produces an audible alarm upon either of the indicators 91 and 92 displaying a hazardous level. Preferably, the alarm 94 provides distinctive audio alarms for the indicators 91 and 92. For example, an alarm from the indicators 91 indicating a hazardous level of carbon dioxide ($CO_2$) and/or volatile organic compound (VOC) may produce a beeping alarm whereas an alarm from the indicators 92 indicating a hazardous level of 2.5 micron particles may produce a continuous alarm. The alarm 94 may be disabled by a switch 54 located on the housing 12.

The electronic circuit 90 contains a wireless transmitter 110 for transmitting data from said particle counter 80 and the solid-state temperature and humidity sensor 103 and the carbon dioxide ($CO_2$) and/or volatile organic compound (VOC) sensor 104 to a remote location. In this example, the wireless transmitter 110 for transmitting data from said particle counter 80 and the solid-state temperature and humidity sensor 103 and carbon dioxide (CO$_2$) sensor and/or volatile organic compound (VOC) sensor 104 to the thermostat 16 as indicated by the arrow 10 in FIG. 1. For example, in the event the particle counter 80 abnormal levels of particles within the 2.5-micron size range or an excessive amounts of carbon dioxide (CO$_2$) and/or volatile organic compound (VOC) while the room temperature is within the desired range, the electronic circuit 90 will actuated the fan 86 in the air conditioning and heating system 15 to reduce the level of particles within the 2.5-micron size range or to reduce or an excessive amounts of carbon dioxide (CO$_2$) and/or volatile organic compound (VOC) in the room 14.

In the alternative, the wireless transmitter 110 for transmitting data history and analytics tools to any remote location. The wireless transmitter 110 provides communications and data flow analysis was completed so that the particle counter 80 is now capable of communicating continuously with BMS, SCADA and other industrial data acquisition and analytics devices and standards.

Although various components can be used with the air quality sensor system 10 the following are an example to enable one skilled in the art to make and use the same. In one example, the particle counter 80 is a Pantower PNS 5003 and the temperature-humidity sensor is a CCS 811 HDC1080. The audible alarm 94 includes a pieso-electric alarm DB Unlimited, Model IP224512-2.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claims is:

1. An air quality sensor system, comprising:
a housing defining a sidewall means;
an internal secondary wall located within said housing;
an air input located on a first sidewall of said sidewall means connected to an air input tunnel extending to said internal secondary wall;
an air output located on a second sidewall of said sidewall means angularly disposed relative to said first sidewall of said sidewall means;
an air output tunnel connecting said internal secondary wall and said air output;
said air output having a cross-sectional area greater than a cross-sectional area of said air input tunnel to ensure a continuous and directed air flow from said air input to be exhausted from said air output; and
a particle counter including a fan located within said housing between said air input tunnel and said air output tunnel for sensing the number of particles passing between said air input and said air output.

2. The air quality sensor system as set forth in claim 1, wherein sidewall means comprises a quadrilateral housing with said second sidewall of said sidewall means disposed perpendicular to said first sidewall of said sidewall means.

3. The air quality sensor system as set forth in claim 1, wherein said housing includes a front end and a rear end with a dividing wall located between said front end and said rear end defining a front region and a rear region; and
a secondary wall separating said front region into a first space and a second space and orientated perpendicular to said dividing wall.

4. The air quality sensor system as set forth in claim 1, wherein said housing includes a front end and a rear end with a dividing wall located between said front end and said rear end defining a front region and a rear region; and
a secondary wall separating said front region into a first space and a second space and orientated perpendicular to said dividing wall; and
said air input tunnel communicating said air input with said second space; and
said air output tunnel communicating said second space with said air output.

5. The air quality sensor system as set forth in claim 1, wherein said air output has a cross-sectional area five (5) times a cross-sectional area of said air input tunnel to ensure a continuous and directed air flow from said air input into said particle counter to be exhausted from said air output.

6. The air quality sensor system as set forth in claim 1, wherein
said air input tunnel is a linear air input tunnel; and
said air output tunnel is a curved output tunnel.

7. The air quality sensor system as set forth in claim 1, wherein said particle counter includes a laser for counting particles passing between said air input and said air output.

8. The air quality sensor system as set forth in claim 1, including an indicator for indicating an undesired count of particles suspended within the air.

9. The air quality sensor system as set forth in claim 1, including a transmitter for transmitting data from said particle counter.

10. The air quality sensor system as set forth in claim 1, including a temperature sensor and a carbon dioxide (CO$_2$) sensor for sensing ambient air.

11. An air quality sensor system, comprising:
a quadrilateral housing having first through fourth sidewalls with a second sidewall disposed perpendicular to a first sidewall;
said housing including a front end and a rear end with a dividing wall located between said front end and said rear end defining a front region and a rear region:
a secondary wall orientated perpendicular to said dividing wall separating said front region into a first space and a second space and, an air input located in said first sidewall connected to an air input tunnel extending to said internal secondary wall;
an air output located in said second sidewall connected to an air output tunnel extending to said internal secondary wall;
said air input tunnel being a linear air input tunnel and said air output tunnel is being a curved output tunnel; and
a particle counter including a fan located within said housing between said air input tunnel and said air output tunnel for sensing the number of particles passing between said air input and said air output.

12. The air quality sensor system as set forth in claim 11, wherein said air output has a cross-sectional area five (5) times a cross-sectional area of said air input tunnel to ensure a continuous and directed air flow from said air input into said particle counter to be exhausted from said air output.

13. The air quality sensor system as set forth in claim 11, wherein said curved output tunnel has cross-sectional area greater than said linear input tunnel.

14. The air quality sensor system as set forth in claim 11, wherein said particle counter includes a laser for counting particles passing between said air input and said air output.

15. The air quality sensor system as set forth in claim 11, including a temperature sensor, a volatile organic compound (VOC) sensor, and a carbon dioxide ($CO_2$) sensor located remote from said first and second sidewalls for sensing ambient air.

16. The air quality sensor system as set forth in claim 11, including an indicator mounted on said housing for indicating an undesired count of particles suspended within the air.

17. The air quality sensor system as set forth in claim 11, including a transmitter for transmitting data from said particle counter.

18. The air quality sensor system as set forth in claim 11,
wherein said air output has a cross-sectional area greater than a cross-sectional area of said air input tunnel to ensure a continuous and directed air flow from said air input into said particle counter to be exhausted from said air output;
said particle counter comprising a laser located on a first surface of said dividing wall for counting particles passing between said air input and said air output;
a transmitter located on a second surface of said dividing wall for transmitting data from said particle counter; and
a front cover a rear cover for enclosing said front end and said rear end of said housing.

\* \* \* \* \*